US006942836B2

(12) United States Patent
Freudenthal et al.

(10) Patent No.: US 6,942,836 B2
(45) Date of Patent: Sep. 13, 2005

(54) SYSTEM FOR FILLING SUBSTRATE CHAMBERS WITH LIQUID

(75) Inventors: Jacob K. Freudenthal, Alameda, CA (US); Donald R. Sandell, San Jose, CA (US)

(73) Assignee: Applera Corporation, Foster City, CA (US)

( * ) Notice: Subject to any disclaimer, the term of this patent is extended or adjusted under 35 U.S.C. 154(b) by 654 days.

(21) Appl. No.: 09/977,225

(22) Filed: Oct. 16, 2001

(65) Prior Publication Data

US 2003/0072681 A1 Apr. 17, 2003

(51) Int. Cl.[7] ........................ G01N 33/00; G01N 15/06; B01L 3/02; B01L 11/00; B01L 3/00

(52) U.S. Cl. ........................... 422/100; 422/50; 422/63; 422/68.1; 422/81; 422/82; 422/101; 422/102; 422/103; 422/104; 436/43; 436/174; 436/180; 137/1; 137/14; 137/15.18

(58) Field of Search ........................... 422/50, 63, 68.1, 422/81, 82, 100, 101, 102, 103, 104; 436/43, 174, 180; 137/1, 14, 15.18

(56) References Cited

U.S. PATENT DOCUMENTS 3,080,759 A 3/1963 McQuaid
3,933,165 A 1/1976 Budzak et al.
4,948,564 A 8/1990 Root et al.
5,210,015 A 5/1993 Gelfand et al.
5,538,848 A 7/1996 Livak et al.
5,780,717 A 7/1998 Wise et al.
5,879,632 A * 3/1999 Demers ...................... 422/100
5,900,130 A * 5/1999 Benvegnu et al. .......... 204/453
5,928,907 A 7/1999 Woudenberg et al.
6,015,674 A 1/2000 Woudenberg et al.
6,086,825 A 7/2000 Sundberg et al.
6,090,251 A 7/2000 Sundberg et al.
6,149,787 A * 11/2000 Chow et al. ................ 204/451
6,159,368 A 12/2000 Moring et al.
6,167,910 B1 1/2001 Chow
6,272,939 B1 * 8/2001 Frye et al. ............... 73/864.81
6,488,897 B2 * 12/2002 Dubrow et al. ............. 422/102
6,514,750 B2 * 2/2003 Bordenkircher et al. . 435/286.2

FOREIGN PATENT DOCUMENTS

DE 197 39 119 A1 3/1999
EP 0 895 240 A1 2/1999
EP 0 955 097 A1 11/1999
EP 1 088 590 A1 4/2001
WO WO 91/17239 11/1991
WO WO 97/36881 10/1997
WO WO 01/28684 A2 4/2001

OTHER PUBLICATIONS

PCT International Search Report for PCT/US02/31574 (filed Oct. 15, 2002), Search completed on Dec. 1, 2002.

(Continued)

*Primary Examiner*—Jill Warden
*Assistant Examiner*—Brian J. Sines

(57) ABSTRACT

The present invention is directed to a system for filling sample chambers with liquid. The system includes a substrate defining the sample chambers and having a fill port, and a network of passageways connecting the sample chambers to the fill port. The system also includes a substrate support to retain the substrate in a fill position and a valve module on the substrate support. The valve module has a fill port seal opening to connect with the fill port of the substrate in the fill position, and a vacuum opening for connection to a source of vacuum. The system further includes a valve body having a liquid outlet port and a vacuum port, and means for operating the valve body so that the liquid outlet port and the vacuum port are alternately in fluid communication with the fill port seal opening.

19 Claims, 5 Drawing Sheets

OTHER PUBLICATIONS

U. Landegren et al., "A Ligase–Mediated Gene Detection Technique," *Science*, 241:1077–80 (Aug. 1988).

D. Nickerson et al., "Automated DNA diagnostics using an ELISA–based oligonucleotide ligation assay," *Proc. Natl. Acad. Sci USA*, 87:8923–27 (Nov. 1990).

P. Grossman et al., "High–density multiplex detection of nucleic acid sequences: oligonucleotide ligation assay and sequence–coded separation," *Nucl. Acids Res.*, 22:4527–34 (1994).

Co–pending U.S. Appl. No. 09/496,408, Inventors: Hon Shin et al. filed Feb. 2, 2000, Title: Apparatus and method for ejecting sample well trays.

Co–pending U.S. Appl. No. 09/848,270, Inventors: Frye et al., filed May 4, 2001, Title: System and method for filling a substrate with a liquid sample.

Co–pending U.S. Appl. No. 09/897,500, Inventors: Borden-kircher et al.,filed Jul. 3, 2001, Title: PCR sample handling device.

Co–pending U.S. Appl. No. 09/606,006, Inventors: Barzilai et al., filed Jun. 29, 2000, Title: Apparatus and method for transporting sample well trays.

* cited by examiner

SYSTEM FOR FILLING SUBSTRATE CHAMBERS WITH LIQUID

BACKGROUND OF THE INVENTION

1. Field of the Invention

This invention relates to filling sample chambers with liquid samples and/or reagents, and, more particularly, to a system for separately filling sample chambers provided in microcard substrates having at least two groups of sample chambers, each group having a network of passageways to connect the sample chambers therein with a group fill port.

2. Description of the Related Art

In the biological testing field, such methods as polymerase chain reaction (PCR), ligase chain reaction, oligonucleotide ligation assay, or hybridization assay are used to detect a reaction of a test sample to an analyte-specific reagent in each a plurality of small detection chambers sometimes referred to in the art as "spots." Typically, an analyte-specific reagent is placed in each detection chamber in advance of conducting the testing method. These analyte-specific reagents in the detection chambers may be adapted to detect a wide variety of analyte classes in the liquid sample, including polynucleotides, polypeptides, polysaccharides, and small molecule analytes, by way of example only. One method of polynucleotide detection is the nuclease process referred to as "TaqMan"® (Roche Molecular Systems, Inc.), conducted during PCR. The above detection methods are well known in the art. They are described in detail in the following articles and patents: U.S. Pat. No. 5,210,015 of Gelfand et al.; U.S. Pat. No. 5,538,848 of Livak et al.; WO 91/17239 of Barany et al. published on Nov. 14, 1991; "A Ligase-Mediated Gene Detection Technique" by Landegren et al published in Science 241:1077–90 (1988); "High-density multiplex detection of nucleic acid sequences: oligonucleotide ligation assay and sequence-coded separation" by Grossman et al., published in Nucleic Acid Research 22:4527–34 (1994); and "Automated DNA diagnostics using an ELISA-based oligonucleotide ligation assay" by Nickerson et al., published in Proc. Natl. Acad. Sci. USA 87:8923–27 (1990).

While the biological testing science has achieved a highly sophisticated state of development, the mechanisms required for the practice of the above-mentioned testing methods efficiently and accurately are of relatively recent vintage. For example, a substrate for simultaneously testing a large number of analytes, which has a small sample size and a large number of detection chambers, has been described in published PCT International Application, WO 97/36681, assigned to the assignee of the present application, the disclosure of which is incorporated herein by reference.

Also, in a commonly assigned and published PCT International Application, WO 01/28684, the complete disclosure of which is incorporated by reference, a further development of a card-like substrate having a plurality of sample detection chambers is disclosed together with a system for filling the substrate with a liquid sample to react with reagents located in the sample detection chambers during thermal cycling of a PCR process. Such card-like substrates are a spatial variant of the micro-titer plate and are sometimes referred to as "microcards." They typically contain 96, 384, or more, individual sample chambers, each having a volume of about 1.0 $\mu$L or less in a card size of 7 cm×11 cm×0.2 cm, for example.

The system for filling substrates disclosed in WO 01/28684 with liquid samples involves first evacuating the sample chambers and network of passageways connecting them with a fill port, and then allowing the liquid to flow into the fill port essentially under the differential in pressure between the evacuated chambers and passageways and atmospheric pressure. In so filling the sample chambers with a liquid sample, for example, it is desirable that gaseous components contained in the liquid be prevented from passing into the substrate, particularly as bubbles that result in a less than complete filling of the substrate with liquid. The filling system disclosed in WO 01/28684 includes a "priming" arrangement to minimize the presence of gas entering the substrate.

SUMMARY OF THE INVENTION

To attain the advantages and in accordance with the purpose of the invention, as embodied and broadly described herein, according to one aspect, the invention comprises a system for filling sample chambers with liquid. The system includes a substrate defining the sample chambers and having a fill port, and a network of passageways connecting the sample chambers to the fill port. The system also includes a substrate support to retain the substrate in a fill position and a valve module on the substrate support. The valve module has a fill port seal opening to connect with the fill port of the substrate in the fill position, and a vacuum opening for connection to a source of vacuum. The system further includes a valve body having a liquid outlet port and a vacuum port, and means for operating the valve body so that the liquid outlet port and the vacuum port are alternately in fluid communication with the fill port seal opening.

According to another aspect, the invention comprises a system for filling sample chambers with liquid samples and/or liquid reagents. The substrate defines at least two groups of the sample chambers, a fill port for each of the at least two groups, and at least two networks of passageways connecting the at least two groups of sample chambers to the respective fill ports. The system further includes at least two valve members associated respectively with the fill ports, each valve member including a housing component having a fill port seal opening and a vacuum opening for connection to a source of vacuum, and a valve body having a liquid outlet port and a vacuum port. The system also includes means for operating the at least two valve members so that the respective liquid outlet port and the vacuum port of each valve body in use is alternately in fluid communication with the fill port seal opening thereof.

According to yet another aspect, the invention comprises a system for filling a substrate containing sample chambers with liquid, including a substrate support to retain the substrate in a fill position and a valve module on the substrate support. The valve module has a fill port seal opening to connect with the fill port of the substrate in the fill position, a vacuum opening for connection to a source of vacuum, and also a valve body having a liquid outlet port and a vacuum port. The system further includes means for operating the valve body so that the liquid outlet port and the vacuum port are alternately in fluid communication with the fill port seal opening.

It is to be understood that both the foregoing general description and the following detailed description are exemplary and explanatory only and are not restrictive of the invention, as claimed.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the present preferred exemplary embodiments of the invention, examples of which are illustrated in the accompanying drawings. Wherever possible, the same reference numbers will be used throughout the drawings to refer to the same or like parts.

In accordance with the present invention, a system for filling sample chambers with liquid samples and/or reagents, in which the sample chambers are defined by a substrate having a fill port and a network of passageways connecting the sample chambers to the fill port. The system is applicable to substrates that differ in construction, numbers of sample chambers, and the arrangement of sample chambers in a given substrate.

Figure 1A:
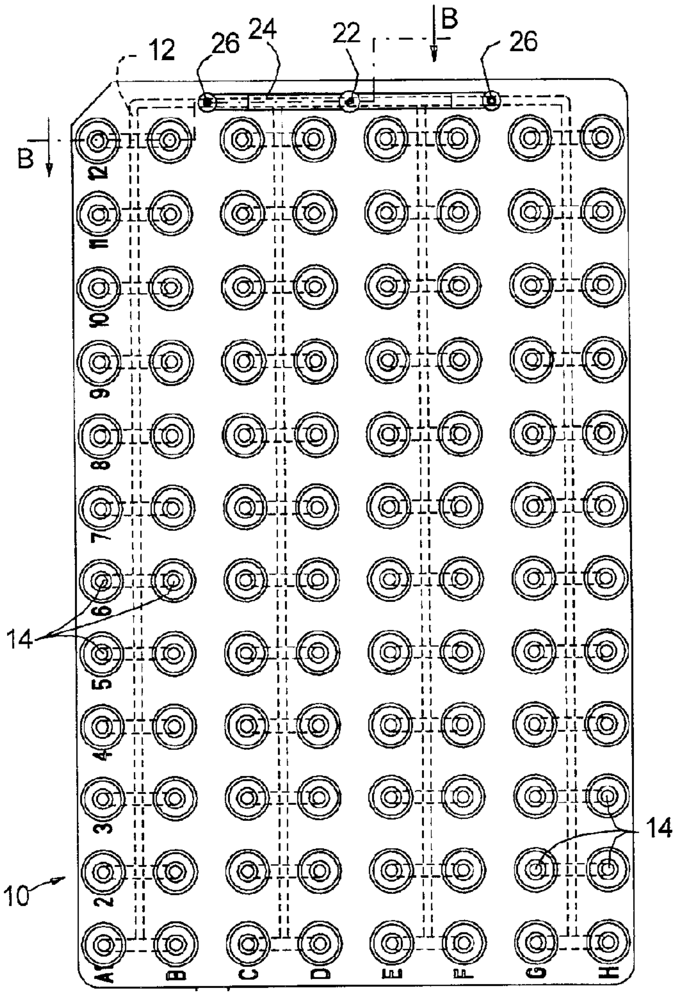
FIG. 1A is a plan view of a substrate used with the system of the present invention.
Figure 1B:
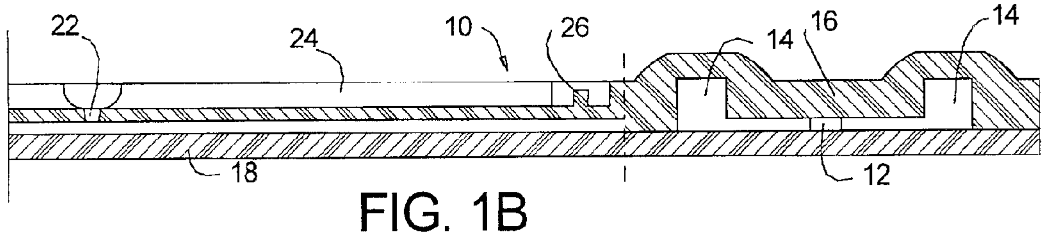
FIG. 1B is an enlarged fragmentary cross section on line B—B of FIG. 1A.

Illustrated in FIGS. 1A and 1B and designated generally by the reference number 10, is a substrate of the type described in WO 1/28684 and available commercially from Applied Biosystems of Foster City, Calif. under the trade designation TaqMan® Human Cytokine Card. The substrate 10 is shown in FIG. 1A as being generally rectangular in shape, and by way of example only, is approximately 7 cm×11 cm×0.2 cm. The substrate 10 defines a network of passageways 12 including a plurality of sample chambers 14. Each sample chamber can hold a predefined volume of liquid sample, such as, for example, approximately 1 $\mu$l. This volume can be varied depending on the specific application.

As shown in FIG. 1B, the substrate 10 is preferably formed as including a top plate 16 and a bottom plate 18. The top and bottom plates 16 and 18 can be joined to each other by a variety of methods. The top and bottom plate should be sealingly joined so that the network of passageways may come under a vacuum when a vacuum source is applied to the substrate. Moreover, the plates 16 and 18 should be joined so that the liquid sample does not leak from the substrate. Typically, the top and bottom plates are bonded together using ultrasonic welding. Other suitable methods such as the use of adhesives, pressure sealing, or heat curing may also be used.

As embodied herein and shown in FIGS. 1A and 1B, the substrate 10 is provided with a fill port 22 for the introduction of liquid into the network of passageways 12 and sample chambers 14. The fill port 22 is located in the center of an attachment/bladder groove 24, in one plate, such as top plate 16 of the substrate 10, and extends through the bottom of the attachment/bladder groove 24. The attachment/bladder groove 24 extends across a portion of the width of the top surface of the substrate plate 16 in an end region of the substrate 10 outside of the sample detection chambers 14. The attachment/bladder groove 24 is slightly recessed from the upper surface of the top plate 16 and includes at opposite ends thereof, a pair of locating pins 26, the function of which will be described in more detail below.

The top and bottom plates 16 and 18 may be made out of any suitable material that can be manufactured according to the required specifications, can withstand any temperature fluctuations that may later occur, i.e., during thermal cycling or other operations performed on the substrate, and can be suitably joined. In addition, for real time optical detection of liquid samples during thermal cycling, the top of each sample detection chamber 14 is preferably optically transparent for detection of the reaction. For this purpose, silica-based glasses, quartz, polycarbonate, or any optically transparent plastic layer, for example, may be used. For use in PCR reactions, the material should be PCR compatible, and the material should preferably be substantially fluorescence free. In one embodiment, the material for the top plate is a polycarbonate manufactured by "BAYER"™, referred to as FCR 2258-1112 and the material for the bottom plate is a 0.015 inch thickness polycarbonate manufactured by "BAYER"™, referred to as Makrofol DE1-1D.

An analyte-specific reagent is typically placed in each sample chamber 14 prior to assembly of the top and bottom plates 16 and 18. However, such reagents may be introduced into the sample chambers through the fill port 22 as a liquid solution after the top and bottom plates are assembled and allowed to dry, leaving the reagent(s) in the chambers as a powder-like residue.

Figure 2B:
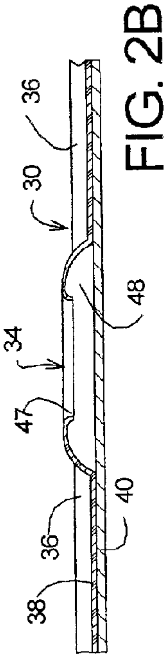
FIG. 2B is an enlarged fragmentary cross section on line B—B of FIG. 2A.
Figure 2:
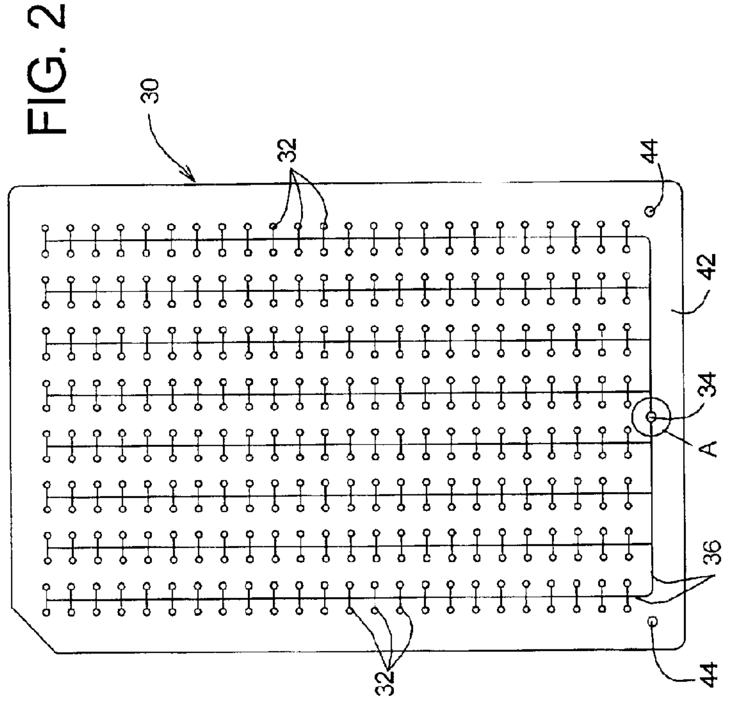
FIG. 2 is a plan view of another substrate used with the system of the present invention.
Figure 2A:
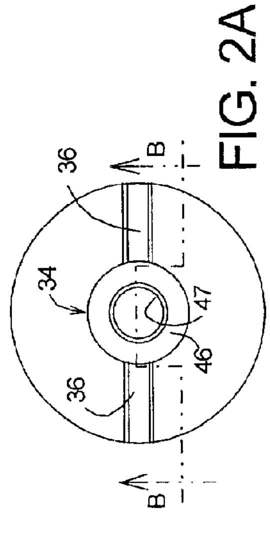
FIG. 2A is an enlarged plan view of the fill port of FIG. 2.

In FIGS. 2–2B, a substrate, representing an alternative to the substrate 10 of FIGS. 1A and 1B, is designated generally by the reference number 30. The substrate 30 contains three hundred and eighty-four (384) sample chambers 32 connected with a fill port 34 via a network of passageways 36. The sample chambers 32, the fill port 34, and the network of passageways 36 are molded or otherwise formed as embossments in a top layer 38 of pliable and transparent plastic film. A bottom layer 40 of aluminum foil is suitably secured to the bottom of the top layer 38 by adhesives, for example. The combined thickness of the two layers 38 and 40 in areas of the substrate 30, other than areas occupied by the chambers 32 and network of passageways 36, is on the order of less than 0.5 mm. The area occupied by the sample chambers 32 and passageways 36 is about 11 cm×6.8 cm or essentially the same as the outside dimensions of the substrate 10 of FIGS. 1A and 1B. However, a peripheral margin 42 enlarges the total area of the substrate 30 to about 12.6 cm×8.4 cm.

As shown in FIG. 2, a pair of guide holes 44 is located in the margin 42 at opposite ends of the substrate 30 outside of the area or region containing the chambers 32 and the passageways 36. The guide holes 44 and 46 open through the top and bottom layers 38 and 40 of the substrate 30 and function in a manner that will be described in more detail below.

As shown in FIG. 2B, the fill port is defined by a dome-like formation 46 in the top layer 38 and having a central opening 47 that is spaced from the bottom layer. A chamber 48 is thus provided under the dome-like formation 46 and through which fluid may pass between the opening 47 and the passageways 36.

Figure 3:
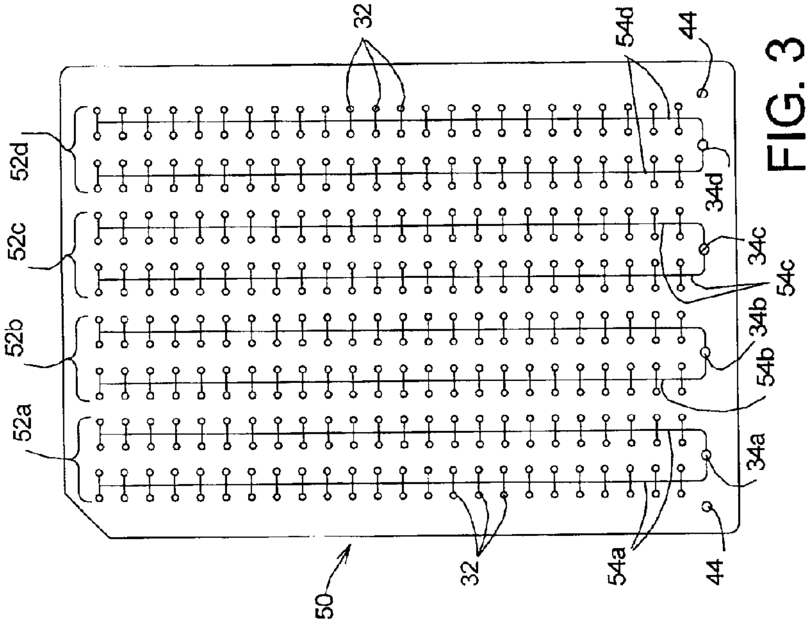
FIG. 3 is a plan view of yet another substrate used with the system of the present invention.

In FIG. 3, another substrate is designated generally by the reference number 50 and is a variant of the substrate 30 of FIG. 2. Although the construction of the substrate 50 is essentially the same as the substrate 30 of FIG. 2, in this instance, four groups 52*a,* 52*b,* 52*c,* and 52*d* of the sample chambers 32 are independently connected by respective passageway networks 54*a,* 54*b,* 54*c* and 54*d* to separate fill ports 34*a,* 34*b,* 34*c,* and 34*d,* each of which is identical to the fill port 34 described above with reference to FIG. 2B.

The substrate 50 of FIG. 3 enables simultaneous processing of multiple samples in a single substrate when the same reagent is present in each of the multiple groups of sample chambers, or simultaneous processing of the same sample with multiple reagents when different reagents are present in each of the respective groups. Also, although four groups of sample chambers are included in the illustrated substrate 50, two, three or more than four groups may be used without departure from the concept represented by that substrate.

In accordance with the present invention, the system for filling sample chamber with liquid includes a substrate support to retain the substrate in a fill position, a valve module on the substrate support and having a fill port seal opening to connect with the fill port of the substrate in the fill position. The valve module further includes a vacuum opening for connection to a source of vacuum, a valve body having a liquid outlet port and a vacuum port, and means for operating the valve body so that the liquid outlet port and the vacuum port are alternately in fluid communication with the fill port seal opening.

Figure 4:
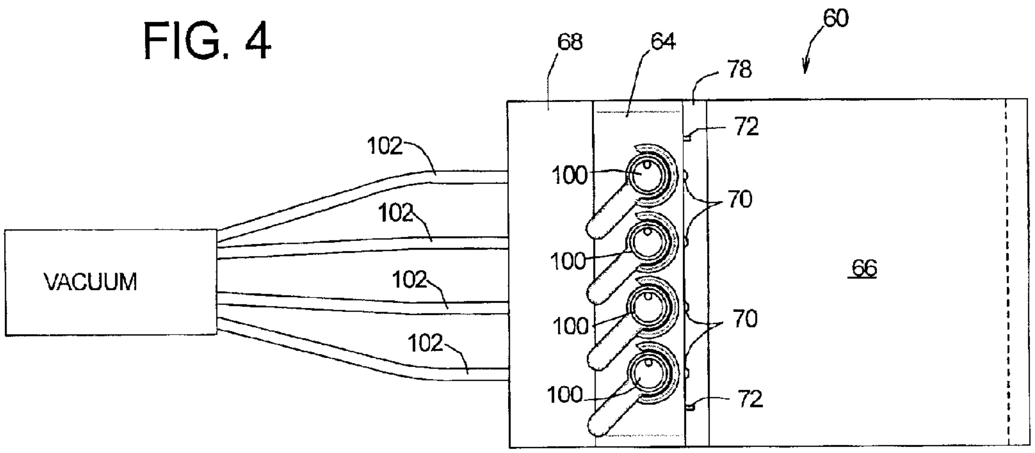
FIG. 4 is a plan view of a substrate support used in the system of the present invention.
Figure 5:
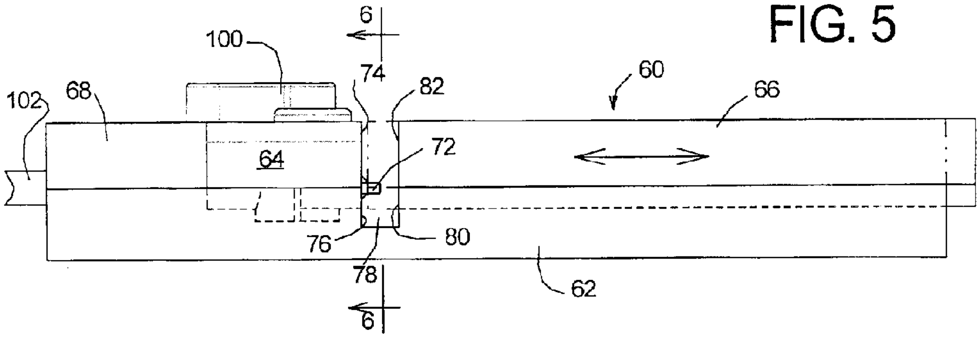
FIG. 5 is a side elevation of the substrate support shown in FIG. 4.
Figure 6:
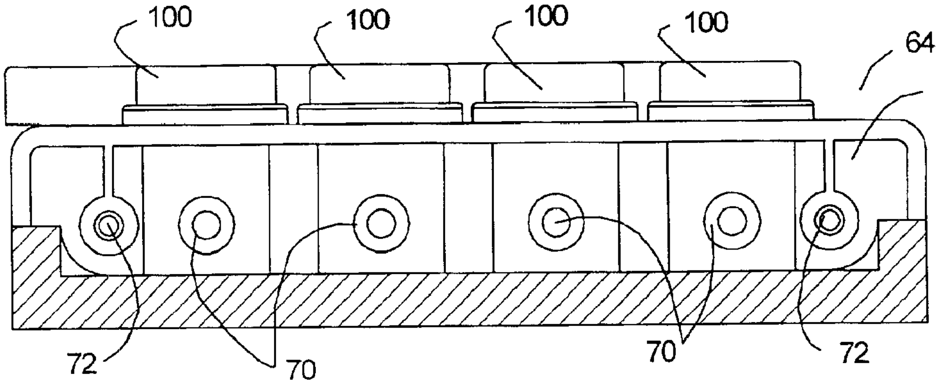
FIG. 6 is a cross section on line 6—6 of FIG. 5.

In the embodiment illustrated in FIGS. 4–6, a substrate support, generally designated by the reference number 60, includes a base 62, a valve module 64, a slidable clamp 66, and a vacuum hose cover 68. Fill port seal openings 70 and substrate locator pins 72 project from a front side 74 of the valve module, which lies flush with a rear face 76 of a substrate receiving channel 78 extending laterally across the base 62. A front face 80 of the channel 78 is spaced from the rear face 76 by a distance sufficient to allow an end edge of a substrate 10, 30, or 50 to pass freely into the channel 78 in front of the projecting fill port seal openings 70 and locator pins 72 when the slidable clamp 66 is retracted to the position depicted by solid lines in FIG. 5 and so that a clamping end 82 thereof lies flush with the front face 80 of the channel 78. Clamp 66 may be moved into and out of a clamping position by a cam-type mechanism known in the art actuated by air pressure from an air cylinder, or actuated by a solenoid valve and motor. Clamp 66 may also be moved by any other means known to one of skill in the art.

Figure 5A:
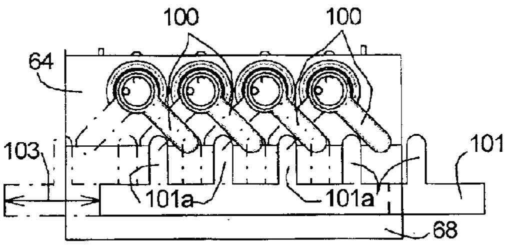
FIG. 5A is a plan view of a comb element for controlling the movement of the valve members of FIG. 4.

FIG. 5*a* shows a comb 101 for controlling the movement of valve members 100. Comb 101 may be slidably mounted onto hose cover 68 to allow for one or more of valve members 100 to be actuated at one time by an actuation means 103. Comb 101 should have a number of teeth, or tooth-like projections, 101*a* at least equal to one more than the number of valve members 100 to be controlled. In the embodiment of FIG. 5*a* there are five teeth 101*a*. With this configuration, sliding of comb 101 from the position depicted with an unbroken line, to the left, depicted with a broken line, by actuation means 103, causes the four rightmost teeth 101*a* to come in contact with the valve members 100 and move them from a closed position to a fill position. The valve members 100 may then all be returned simultaneously to a closed position by sliding comb 101 back to the right.

The valve module 64 includes a frame 98 adapted to seat, such as, for example, by press fit, into the base 62 in front of the vacuum hose cover 68 as shown in FIGS. 4 and 5. The frame 98 carries one valve member 100 associated with each fill port seal opening 70; or four such valve members in the module 64 shown in FIGS. 4 and 6. A vacuum hose 102 extends from each valve member 100 to a source vacuum 104.

Figure 7:
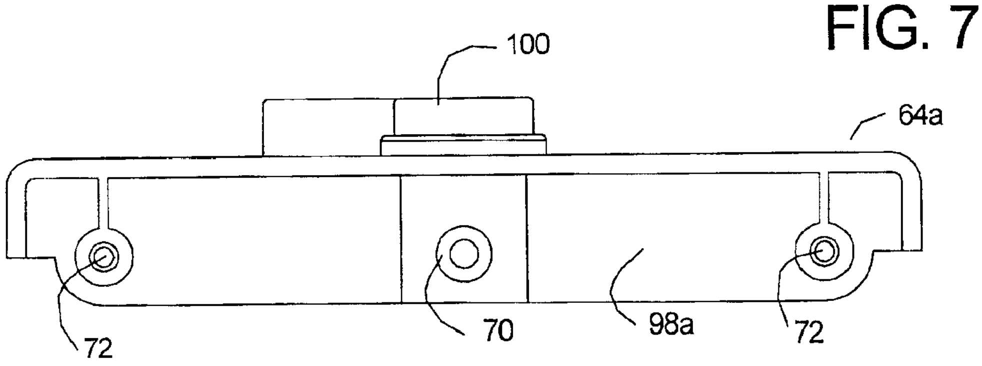
FIG. 7 is a front elevation of an alternative valve module of the present invention.
Figure 8:
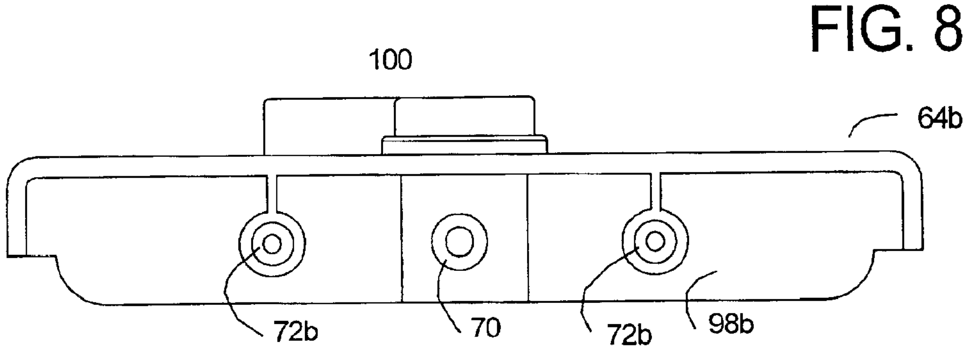
FIG. 8 is front elevation of another alternative valve module of the present invention.

To accommodate different types of substrates, such as the substrates 10, 30 and 50 described above, the valve module 64 is interchangeable with valve modules 64*a* and 64*b* shown in front elevation in FIGS. 7 and 8, respectively. Thus, the valve module 64, as mentioned above, includes four fill port seal openings 70 to register with the respective fill ports 34*a*–34*b* of the substrate 50 described above with reference to FIG. 3. The locator pins 72 on the module 64 engage in the guide holes 44 of the substrate 50 to ensure accurate registration of the fill ports therein with the fill port seal openings 70 on the module 64.

The module 64*a* of FIG. 7 is the same as the module 64 of FIG. 6 in all respects except that only one fill port seal opening is provided to register with the fill port 34 of the substrate 30 shown in FIG. 2. The valve module 64*b* of FIG. 8 is used with the substrate 10 of FIGS. 1A and 1B. As such, it includes a single fill port seal opening 70 to register with the fill port 22 of the substrate 10, and a pair of locator sockets 72*b* to engage the locator pins 26 in the substrate 10.

Figure 9:
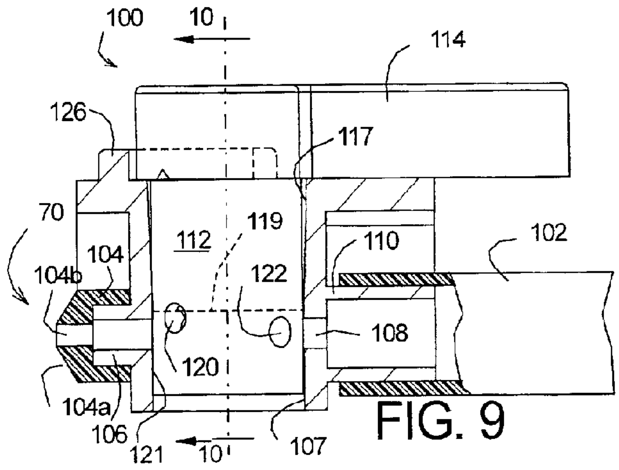
FIG. 9 is a vertical cross section of a valve member of the present invention.
Figure 10:
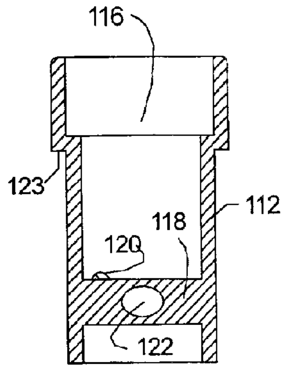
FIG. 10 is a cross section on line 10—10 of FIG. 9.

An embodiment of the valves 100, which are of the same construction, is shown in FIGS. 9 and 10. The fill port seal opening, as shown in FIG. 9, includes an elastomeric tip 104 fixed to the front end of a nipple 106 that opens radially to a circular bore 107 in the frame 98, 98*a*, 98*b* of the valve module 64, 64*a*, 64*b*. The tip 104, in the illustrated embodiment, is formed with a frusto-conical front-end 104*a* and a central bore 104*b*. A vacuum opening 108 is diametrically opposite from the nipple 106 and extends from the bore 107 to a vacuum hose nipple 110.

Figure 9A:
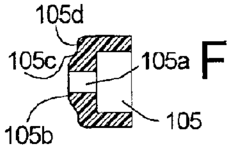
FIG. 9A is a longitudinal cross-section of an alternative elastomeric tip for the valve shown in FIG. 9.

In FIG. 9A, an alternative elastomeric tip 105 is shown. Tip 105 has a central bore 105*a* that opens through a central front annulus 105*b*. Tip 105 also has a frusto-conical surface 105*c* that diverges from the central front annulus 105*b* to a peripheral annulus 105*d*.

In accordance with the invention, the valve body comprises a cylindrical body rotatable in the bore of the valve module and defines a reservoir for the liquid that is isolated from fluid communication with the vacuum port, has a liquid outlet port and a vacuum port and includes priming means for venting gas from the liquid at the liquid outlet port.

In the illustrated embodiment, and as shown in FIGS. 9 and 10, a cylindrical valve body 112 is positioned for relative angular movement in the bore 107 and includes a radial handle 114 at its top to effect such movement manually. A liquid reservoir 116 is open at the top of the valve body 112 and has a bottom defined by the top surface of a solid bridge portion 118 of the valve body. A liquid outlet port 120 having vertical and radial portions in the bridge portion 118 is located so that major part of the radial portion thereof aligns with the nipple 106 and a minor part of the radial portion opens to the reservoir 116. A vacuum port 122 extends diametrically across the valve body 112 within the solid bridge portion 118 and is displaced angularly from the liquid outlet port 120 by 90 degrees.

As can be seen in FIGS. 9 and 10, the reservoir 116 is configured to communicate with the nipple 106 via the outlet port 120 located at the base of the reservoir 116. The upper portion 117 of the valve bore 107 in the frame 98 is tapered so as to diverge upwardly from a dashed line 119 at the top of a bottom cylindrical portion 121. The outlet port 120 is located on the exterior of the valve body 112 so that a minor portion thereof extends into the tapered upper portion 117 of the valve bore, and thus communicates with the outside atmosphere. Because of this configuration, air is vented during a substrate fill operation to minimize drawing in of gas bubbles that may be present in the liquid contained in the reservoir 116 into the substrate. However, liquid should not leak out of this opening because the portion of the outlet port 120 on the exterior of the valve body 112, that opens to the diverging space between the upper tapered portion 117 and the valve body 112, is so small in relation to the portion of the outlet port 120 that communicates with the nipple 106, that the weight of the liquid inhibits the overcoming of the surface tension of the liquid. The flow path between the reservoir 116 and the fill port seal opening 70 is thus primed or substantially devoid of gas.

In addition to priming feature, the tapered upper portion 117 of the bore restricts contact between the valve body 112 and the bore 107 to the bottom cylindrical portion 119, thus reducing friction tending to oppose rotation of the valve body 112 in the bore. To support the upper portion of the valve body 112 and to locate the outlet port 120 thereof in relation of the bottom of the tapered portion 117 of the bore 107, a seating shoulder 123 on the valve body bears on the top surface of the frame 98 surrounding the bore 107.

Figure 11:
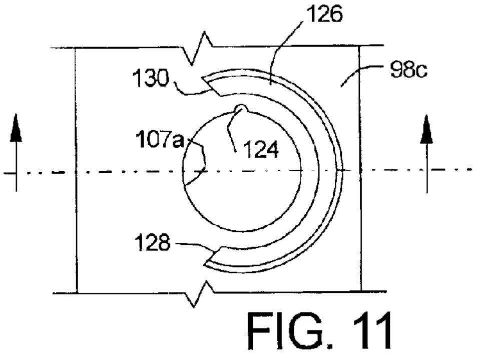
FIG. 11 is fragmentary plan view of an alternative valve module frame used with the present invention.
Figure 12:
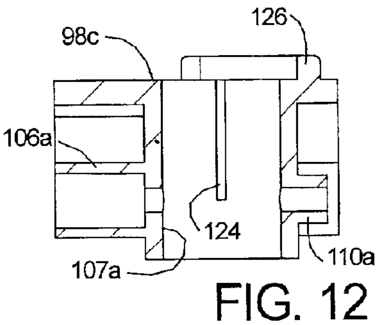
FIG. 12 is a cross section on line 12—12 of FIG. 11.

One alternative embodiment of the priming feature is shown in FIGS. 11 and 12. In this instance, the bore 107*a* is wholly cylindrical to fully complement the valve body 112 and is formed with a vertical vent channel 124 that aligns with the valve outlet port 120 when the valve body 112 is positioned with the vacuum port 122 in communication with the fill port seal opening 70 (FIG. 13B). As in the previous embodiment, surface tension of the liquid inhibits passage of the liquid into the vent channel 124.

Figure 13A:
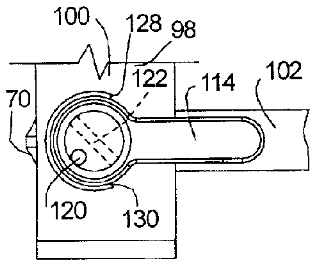
FIG. 13A is a plan view of a valve member of the present invention in a closed point.
Figure 13B:
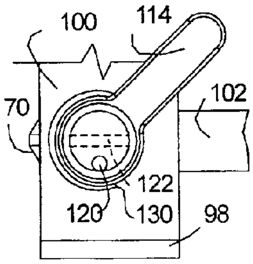
FIG. 13B is a plan view of a valve member of FIG. 13A a vacuum position.
Figure 13C:
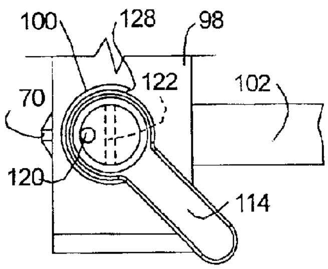
FIG. 13C is a plan view of a valve member of FIG. 13A in a fill position.

FIGS. 13A–13C depict three operational positions of a valve member 100 to fill the reservoir 116 with liquid, evacuate the chambers 14, 32 of a substrate 10, 30, 50, and fill the chambers 14, 32 with liquid, respectively. To establish these respective positions of a valve member 100, an arcuate valve stop wall 126, having end stops 128 and 130, is located concentrically around the bore 107, 107*a*. Thus, in the closed position of the valve member 100 shown in FIG. 13A, the valve handle 114 is midway between the end stops 128 and 130 and the reservoir 116 is isolated from the fill port seal opening 70 to receive the liquid to be introduced into a substrate. In FIG. 13B, when the handle 114 abuts the end stop 128, the vacuum port 122 connects the fill port seal opening 70 to the vacuum hose 102. With the fill port seal opening 70 in communication with a fill port 22, 34 of a substrate, this position of the valve member 100 will reduce pressure in a substrate to below atmospheric pressure. Thereafter, the valve member 100 is rotated until the handle 114 thereof engages the end stop 130 (FIG. 13C) to place the outlet port 120 in communication with the fill port seal opening 70 and the substrate interior and fill the chambers thereof with liquid under a pressure corresponding to the differential between the evacuated substrate chambers and atmospheric pressure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for filling sample chambers with liquid, comprising:

a substrate defining the sample chambers, a fill port, and a network of passageways connecting the sample chambers to the fill port;

a substrate support to retain the substrate in a fill position; and a valve module on the substrate support, the valve module having a fill port seal opening to connect with the fill port of the substrate in the fill position, and a vacuum opening for connection to a source of vacuum, and further including a valve body having a liquid outlet port and a vacuum port, wherein the valve body comprises a cylindrical body rotatable in a bore of the valve module.

2. The system of claim 1, wherein the top portion of the cylindrical body defines a reservoir for the liquid, the reservoir being isolated from fluid communication with the vacuum port.

3. The system of claim including priming means for venting gas from the liquid at the liquid outlet port.

4. The system of claim 3, wherein the priming means comprises a divergence of the bore of the valve module and the cylindrical body upwardly from a minor portion of the liquid outlet port.

5. The system of claim 3, wherein the priming means comprises a surface groove in the bore of the housing component that communicates with the liquid outlet port when the vacuum port is in fluid communication with the fill port seal opening.

6. The system of claim 1, wherein the substrate includes at least two groups of the sample chambers, a fill port for each of the at least two groups, and at least two networks of passageways connecting the at least two groups of sample chambers to the respective fill ports, and wherein the valve module includes at least two fill port seal openings associated respectively with the at least two fill ports, and at least two valve bodies each having a liquid outlet port and a vacuum port, wherein the at least two valve bodies comprises means for simultaneously actuating the at least two valve bodies comprising a reciprocal comb member having tooth-like valve handle engaging projections exceeding the number of valve bodies by one.

7. A system for filling sample chambers with liquid samples and/or liquid reagents, comprising:

a substrate defining at least two groups of the sample chambers, a fill port for each of the at least two groups, and at least two networks of passageways connecting the at least two groups of sample chambers to the respective fill ports;

at least two valve members associated respectively with the fill ports, each valve member including a housing component having a fill port seal opening and a vacuum opening for connection to a source of vacuum, and a valve body having a liquid outlet port and a vacuum port, wherein the housing components of the at least two valve members are integrated in a common valve housing with front and back sides, the fill port seal openings for the at least two valve members being aligned on the front side of the common valve housing, and the vacuum port openings being accessible at the back side of the common valve housing.

8. The system of claim 7 including means for clamping the substrate against the front side of the common valve housing so that the fill ports for the at least two groups of sample chambers are aligned with and sealed against the fill port seal openings of the respective valve members.

9. A system for filling sample chambers with liquid samples and/or liquid reagents, comprising:

a substrate defining at least two groups of the sample chambers, a fill port for each of the at least two groups, and at least two networks of passageways connecting the at least two groups of sample chambers to the respective fill ports;

at least two valve members associated respectively with the fill ports, each valve member including a housing component having a fill port seal opening and a vacuum opening for connection to a source of vacuum, and a valve body having a liquid outlet port and a vacuum port, wherein the valve body of the at least two valve members comprises a cylindrical body rotatable in the respective housing component, the vacuum port being defined by a diametric hole through the cylindrical body.

10. The system of claim 9, wherein the top portion of the cylindrical body defines a reservoir for the liquid samples and/or liquid reagents.

11. The system of claim 10, wherein the liquid outlet port extends radially from the reservoir to a peripheral surface of the cylindrical body and is angularly spaced from the diametric hole.

12. The system of claim 10, wherein the means for operating the at least two valve members comprises a radial handle on the cylindrical body of each of the valve members, and angularly spaced stops for positioning either of the vacuum port or the liquid outlet port in fluid communication with the respective fill port seal opening.

13. A system for filling a substrate containing sample chambers and a fill port with liquid, comprising:

a substrate support to retain the substrate in a fill position;

a valve module on the substrate support, the valve module having a fill port seal opening to connect with the fill port of the substrate in the fill position, a vacuum opening for connection to a source of vacuum, and a valve body having a reservoir for the liquid, a liquid outlet for connecting the reservoir to the fill port seal opening, and a vacuum port; and means for operating the valve body so that the liquid outlet port and the vacuum port are alternately in fluid communication with the fill port seal opening.

14. The system of claim 13, wherein the reservoir is isolated from fluid communication with the vacuum port.

15. The system of claim 13, further comprising priming means for venting gas from the liquid at the liquid outlet port.

16. The system of claim 15, wherein the priming means comprises a divergence of the bore of the valve module and the cylindrical body upwardly from a minor portion of the liquid outlet port.

17. The system of claim 15, wherein the priming means comprises a surface groove in the bore of the housing component that communicates with the liquid outlet port when the vacuum port is in fluid communication with the fill port seal opening.

18. The system of any one of claims 2, 7, 9, 13, wherein the fill port seal opening is defined by an elastomeric tip having a central bore and a rearwardly divergent frusto-conical surface.

19. The system of claim 18, wherein the rearwardly divergent frusto-conical surface extends between a central front annulus and a peripheral front annulus.

* * * * *